United States Patent [19]
Peterson

[11] Patent Number: 6,143,563
[45] Date of Patent: Nov. 7, 2000

[54] CRYOPRESERVATION OF EMBRYOGENIC CALLUS

[75] Inventor: David Jay Peterson, Ames, Iowa

[73] Assignee: Pioneer Hi-Bred International, Inc., Des Moines, Iowa

[21] Appl. No.: 08/859,313

[22] Filed: May 20, 1997

[51] Int. Cl.[7] .............................. C12N 5/00; C12N 5/02; C12N 5/04
[52] U.S. Cl. ....................... 435/430.1; 435/410; 435/412; 435/420; 435/424; 435/431
[58] Field of Search ..................................... 435/412, 420, 435/424, 431, FOR 114, FOR 115, FOR 116, FOR 118, FOR 122, 410, 430.1

[56] References Cited

U.S. PATENT DOCUMENTS

| | | | |
|---|---|---|---|
| 4,615,141 | 10/1986 | Janick et al. | 47/57.6 |
| 4,777,762 | 10/1988 | Redenbaugh et al. | 47/57.6 |
| 5,183,757 | 2/1993 | Roberts | 435/240.49 |
| 5,464,769 | 11/1995 | Attree et al. | 435/240.4 |
| 5,596,131 | 1/1997 | Horn et al. | 800/205 |

FOREIGN PATENT DOCUMENTS

| | | | |
|---|---|---|---|
| 40 13 099 A1 | 10/1991 | Germany | C12N 15/82 |
| WO 93/14191 | 7/1993 | WIPO | C12N 5/00 |
| WO 95/06128 | 3/1995 | WIPO | C12N 15/82 |

OTHER PUBLICATIONS

Withers, Lindsey A., "Long–Term Preservation of Plant Cells, Tissues and Organs", *Oxford Surveys of Plant Molecular and Cell Biology*, 4: 221–272 (1987).

McLellan et al., "The Responces of Four Cultured Plant Cell Lines to Freezing and Thawing in the Presence or Absence of Cyroprotectant Mixtures", *Cyro–Letters*, 11: 189–204 (1990).

Bachiri et al., "Successful cryopreservation of suspension cells by encapsulation–dehydration", *Plant Cell, Tissue and Organ Culture*, 43: 241–248 (1995).

Dumet et al., "Cryopreservation of oil palm (*Elaeis guineensis* Jacq.) somatic embryos involving a desiccation step", *Plant Cell Reports*, 12: 352–355 (1993).

Sakai et al., "Cryopreservation of nucellar cells of navel orange (*Citrus sinensis* Osb.) by a simple freezing method", *Plant Science*, 74: 243–248 (1991).

Shimonishi et al., "Cryopreservation of melon somatic embryos by desiccation method", *Japan J. Breed*, 41: 347–351 (1991).

Uragami et al., "Cryopreservation of Microspore Embryos of Oilseed Rape (*Brassica Napus* L.) by Dehydration in Air with or Without Alginate Encapsulation", *Cryo–Letters*, 14: 83–90 (1991).

Dereuddre et al., "Resistance of Alginate–Coated Somatic Embryos of Carrot (*Daucus Carota* L.) to Desiccation and Freezing in Liquid Nitrogen: 1. Effects of Preculture", *Cryo–Letters*, 12: 125–134 (1991).

Scottez et al., "Cryopreservation of Cold–Acclimated Shoot Tips of Pear in Vitro Cultures after Encapsulation–Dehydration", *Cryobiology*, 29: 691–700 (1992).

Paulet et al., "Cryopreservation of apices of in vitro plantlets of sugarcane (*Saccharum sp.* hybrids) using encapsulation/dehydration", *Plant Cell Reports*, 12: 525–529 (1993).

Niino et al., "Cryopreservation of alginate–coated in vitro–grown shoot tips of apple, pear and mulberry", *Plant Science*, 87: 199–206 (1992).

Compton et al., "Plant Recovery from Maize Somatic Embryos Subjected to Controlled Relative Humidity Dehydration", *In Vitro Cell Dev. Biol.*, 28P: 197–201 (1992).

DiMaio et al., "Cryopreservation Technology for Plant Cell Cultures", *Journal of Tissue Culture Methods*, vol. 12, No. 4, 163–169 (1989).

Withers et al., "Proline: A Novel Cryoprotectant for the Freeze Preservation of Cultured Cells of *Zea mays* L", *Plant Physiol.*, 64: 675–678 (1979).

Songstad, et al., "Establishment of Friable Embryogenic (Type II) Callus from Immature Tassels of *Zea Mays* (Poaceae)", *American Journal of Botany*, 79(7): 761–764 (1992).

Uragami, Atsuko, "Cryopreservation of Asparagus (*Asparagus officinalis* L.) cultured in vitro", *Res. Bull. Hokkaido Natl. Agric. Exp. Stn.*, 156: 1–37 (1991).

Benson, Erica, "Cryopreservation", *Plant Cell Culture—Practical Approach Series*, 147–167 (1994).

*Primary Examiner*—David M. Naff
*Assistant Examiner*—Deborah K. Ware

[57] ABSTRACT

A method for cryopreserving plant callus without the use of cryoprotectants or programmable freezers. The callus is spread on a physical support, grown on a media supplemented with an osmoticum, desiccated under controlled conditions, placed directly into cold storage, and can be revived by thawing. Actively growing callus from a number of species can be cryopreserved using the instant invention.

3 Claims, 1 Drawing Sheet

CRYOPRESERVATION OF EMBRYOGENIC CALLUS

TECHNICAL FIELD

This invention relates generally to the field of agriculture and crop production, and more particularly to the production of cryopreserved callus for use in plant transformation methods.

BACKGROUND OF THE INVENTION

Techniques of crop improvement in agriculture involve a search for strains of plants which exhibit new and useful characteristics, or to refine and improve on existing ones. The search has evolved from mere selection of a desirable parent plant, to hybridization between parental strains in which each exhibits desirable characteristics and to cross-breeding between homozygous strains such that identical $F_1$ progeny will be produced in each subsequent crossbreeding.

The conventional methods of maintaining genetic identity are well known and described in the literature. See, e.g., R. W. Allard "Principle of Plant Breeding", (John Wiley and Sons, Inc., 1960). The maintenance of purebred strains and the repeated crossbreeding to obtain $F_1$ progeny are time consuming and labor intensive.

Recent advances in molecular biology have dramatically expanded the ability of scientists to manipulate the germplasm of animals and plants. Genes controlling or contributing to specific phenotypes (for example, genes encoding specific polypeptides that provide antibiotic or herbicide resistance) have been identified within certain germplasm, and have been isolated and characterized. Even more important has been the ability to take the genes which have been isolated from one organism and to introduce them into another organism. This process of transformation can be accomplished even where the recipient organism is from a different phylum, genus or species from that which donated the gene.

Attempts have been made to genetically engineer desired traits into plant genomes by introduction of exogenous genes using genetic engineering techniques. These techniques have been successfully applied in monocotyledonous and dicotyledonous species. The uptake of new DNA by recipient plant cells has been accomplished by various means, including Agrobacterium infection, polyethylene glycol (PEG)-mediated DNA uptake, electroporation of protoplasts, and microprojectile bombardment (for a review see, Songstad, et al., 1995, Plant Cell, Tissue and Organ Culture 40:1–15). Maize transformation is often unreliable or occurs at a fairly low frequency. Any development which could ensure the efficiency of maize transformation would be of tremendous value to the field of crop improvement.

The use of regenerable tissue cultures is well known to those of skill in the art. Plant regeneration from maize callus tissue cultures was first demonstrated by C. E. Green and R. L. Philips in 1975 (Green, et al., 1975, Crop Sci. 15:417–421). Transformation of maize callus can be performed in a variety of ways, including, for example, microprojectile bombardment. It is critical that the tissue used for the transformation, especially in the case of microprojectile bombardment, be of the correct morphology. In maize, Type II or friable callus, at the correct stage physiologically and morphologically, will typically transform at a relatively high efficiency. The difficulty arises in the long term maintenance of Type II callus, for only yellow compact callus that is not watery will transform, and the time required to obtain such callus can be from a few months to a year of subculture (Philips, R. L., et al., In: Sprague, et al. (Eds.), 1988, Corn and Corn Improvement, pp. 345–387, Agronomy, Madison, Wis.). Also, different inbred varieties of maize initiate Type II callus at different rates and are more subject to environmental variation affecting the donor plant and culture conditions (Tomes, D. T., 1985, p. 175–203. In S. W. J. Bright and M. G. K. (Eds.) Advances in agricultural biotechnology: Cereal tissue and cell culture. Nijhoff/Junk, Boston). Cryopreservation of callus would allow one to maintain a supply of regenerable embryogenic cultures, but Type II callus has historically been difficult to cryopreserve (Shillito, R. D., et al., 1994, p. 695–704. In Freeling, M., Walbot, V. (Eds.) The Maize Handbook. Spriger-Verlag, New York). Consequently, being able to capture Type II callus in the most amenable stage for transformation will not only vastly improve the efficiency of transformation but also save the researcher invaluable amounts of time.

Various methods have been described for freezing down plant tissue. In the methods currently available in the art, plant callus is pretreated with sugars or polyols, and a mixture of cryoprotectants (dimehtyl sulfate, proline, sugars, polyols) is applied. This is followed by a slow freezing to −40 degree celsius before quenching in liquid nitrogen and rapid thawing (for a review see, Withers, L. A., 1987, Oxford Surveys of Plant Molecular and Cell Biology, 4:221–272). Such methods require an expensive programmable freezer to obtain adequate results. In addition, cryoprotectants which effect the morphology and physiology of the tissue are typically necessary to prevent lesions which form during freezing and thawing and which subsequently result in cell death (McLellan, et al., 1990, Cryo-Letters 11:189–204). In U.S. Pat. No. 5,596,131, a method for cryopreservafion of embryogenic cell cultures is described. Callus of *Dacrylis glomerata* L. is mixed with a cryoprotectant solution containing glycerol, dimethyl sulfoxide, and proline and then placed in an apparatus which can freeze the callus at a controlled rate. In the published PCT application WO 95/06128, maize embryogenic cells of Type II callus in suspension culture are cryopreserved by adding a cryoprotectant containing dimethyl sulfoxide, polyethylene glycol, proline and glucose to the suspension cultures and then cooling the mixture at a controlled rate at 0.5 degree per minute. Both of these methods introduce cryoprotectants into the cells resulting in undesirable morphological and physiological changes in the callus. In addition, both methods require an expensive programmable freezing apparatus, to control the rate of cooling.

In other, somewhat related methods, somatic embryos have been preserved for use as artificial seeds. In U.S. Pat. No. 4,615,141, Janick and Kitto describe a method of pre-treating embryos with increasing sucrose concentrations or by applying abscisic acid, followed by encapsulation of one or more embryos in a hydrated coating material. In U.S. Pat. No. 4,777,762, Redenbaugh et al. describe a method for producing dessicated analogs of botanic seeds which are created by removing a portion of the water by slow or fast drying so that the plant tissue is no longer saturated with water. In U.S. Pat. No. 5,464,769, Attree and Fowke describe a method of desiccating conifer somatic embryos wherein the embryos are matured, desiccated and then encapsulated. A variety of publications describe preservation of plant cells by encapsulation of plant cells or embryos, preculture in the presence of an osmoticum, and then dessication by placing coated cell in the laminar flow hood or in the presence of silica gel, followed by immersion in liquid nitrogen (Bachiri, et al., 1995, Plant Cell. Tissue and Organ Culture 43: 241–248; Dumet, et al., 1993, Plant Cell Reports 12: 353–355; Sakai, et al., 1991, Plant Science 74: 243–248; Shimonisih, et al., 1991, Japan J. Breed. 41: 347–351; Uragami, et al., 1993, Cryo-Letters 14: 83–90; Dereddre, et al., 1991, Cryo-Letters 12: 125–143; Scottez, et al., 1992, Cryobiology 29: 691–700; Paulet, et al., 1993, Plant Cell Reports 12: 525–529; Niino, et al., 1992, Plant Science 87: 199–206). Maize somatic embryos have been grown on abscisic acid and then subjected to controlled relative humidity dehydration (Compton et al., 1992, In Vitro Cell. Dev. Biol. 28P: 197–201). None of the above methods uses actively growing, transformable plant tissue as described in the present invention. In addition, the present invention does not require encapsulation, the use of a programmable freezer, or cryoprotectants in the freeze mixture.

One of the advantages of the present invention is to allow the scientist to establish a readily transformable callus culture and keep it for long periods. This is especially important when sources of embryos become unavailable or if the scientist finds a line callus that is readily transformable. In addition, the present invention provides a method that allows for preservation of lines that have already been transformed, but for logistical reasons cannot be immediately progressed to callus growth and plant regeneration. Callus lines can now be frozen at any stage of the process from initial generation of a line, maintenance of the pre-transformation or post-transformation, or for sub-culturing. The present invention is simpler and less expensive to perform than earlier methods and can be used on a variety of callus types, unlike other methods.

SUMMARY OF THE INVENTION

Figure 1:
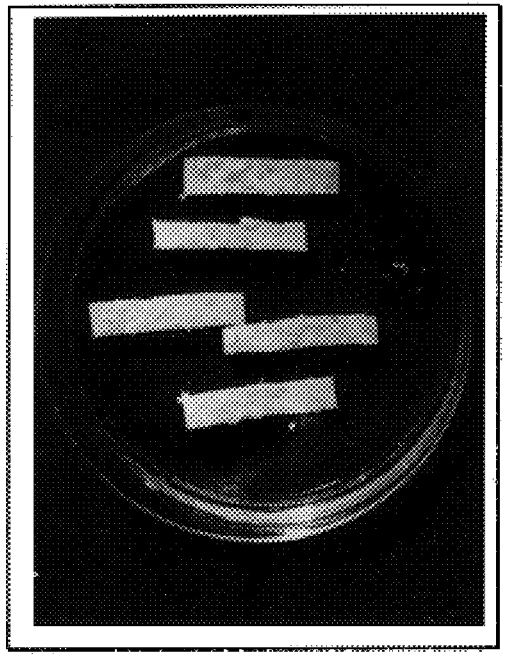
FIG. 1 is a photograph of callus immediately after removal from liquid nitrogen.

The present invention is directed to a method for cryopreserving plant callus that satisfies the need to preserve actively growing, transformable or transformed plant callus without the use of chemicals that can alter the physiology of the cells. Furthermore, by being able to cryopreserve a highly transformable line, this method will permit the recovery of an increased number of recovered transformed events, the entire process from callus isolation to product development is more efficient. Thus, crops of greater agricultural value will be produced at a faster rate.

The method of cryopreserving plant callus comprises spreading the plant callus evenly on a physical support in order to manipulate the fragile callus with minimal damage, growing the plant callus on maintenance media supplemented with an osmoticum to improve viability of the preserved cells, slowly removing the water from the plant callus under controlled conditions, placing the dry plant callus in storage for future use, and reviving the stored plant callus from storage so that the plant callus will begin to grow again. The physical support can be a glass fiber disc, a paper disc, a fine wire mesh, or any similar material. The osmoticum used to improve viability can be mannitol, sucrose, glucose, or any chemical that can function as an osmoticum while still maintaining viability of the cells. In order to desiccate the tissue, the support with the callus can be placed in a chamber in the presence of a saturated solution of $Ca(NO_3)_2 \cdot 4H_2O$, or $(NH_4)_2SO_4$, or in any mechanical device that is capable of altering the ambient humidity. It should be noted that a controlled rate of evaporative dehydration is important for the maintenance of cell viability.

Once the tissue is desiccated, the desiccated tissue can be maintained by submersion in liquid nitrogen, or by placing the plant callus at any temperature between $-80°$ C. to room temperature, depending on how long the tissue is to be stored. In general, the lower the temperature, the longer the tissue will survive. To revive the plant callus for further use, it can be thawed at a variety of temperatures including, for example, room temperature, $4°$ C., $37°$ C., or any temperature which does not decrease cell viability.

In a preferred embodiment of the invention, the method of cryopreserving the plant callus comprises spreading the plant callus evenly on a glass fiber disc, growing the plant callus on a maintenance media supplemented with mannitol and proline, desiccating the plant tissue by placing the tissue in a closed container in the presence of a saturated solution of either $Ca(NO_3)_2 \cdot 4H_2O$ or $(NH_4)_2SO_4$, storing the plant callus in liquid nitrogen, and reviving the stored plant callus by thawing the cells at room temperature.

DETAILED DESCRIPTION OF THE INVENTION

The present invention provides a method for cryopreserving callus tissue and for maintaining the cryopreserved callus for an indefinite period of time. In typical cryopreservation methods currently practiced in the art, callus cells are frozen in liquid cryoprotectants which contain various mixtures of chemicals which protect membranes from damage during cooling and aid in protecting protein and nucleic acids from inactivation (Towill, L. E., 1991, p. 41–70. In J. H. Dodds (Ed.) In Vitro Methods for Conservation of Plant Genetic Resources. Chapman and Hall, London). However, there are significant disadvantages associated with this methodology. Cryoprotectant chemicals often have a toxic effect on the callus cells and can result in undesirable changes in the physiological and morphological state of the cells.

The present invention allows for freezing in the absence of cryoprotectants in the freezing mixture, resulting in a more rapid recovery of the cells with little change in callus morphology. Thus the present invention addresses how to preserve for future use cell lines that have been determined to be particularly amenable to regeneration or high efficiency transformation. The present invention also provides a method that allows for preservation of lines that have already been transformed, but which for logistical reasons cannot be immediately progressed to callus growth and plant regeneration. Lines can now be frozen at any stage of the process from initial generation of a line, maintenance of the line pre-transformation or post-transformation, or for sub-culturing. The skilled practitioner can therefore choose when it is convenient to do experiments, and also not be limited by the availability of lines that are amenable to transformation. Because one is freezing lines previously determined to be highly regenerable or transformable, one is immediately beginning with a source of material that has a higher probability of resulting in larger numbers of transgenic events. The present inventor has observed that independently selected lines can vary by greater than 10-fold in transformation efficiency. A method that begins with cell lines that exhibit a high transformation efficiency can help ensure an immediate improvement in the number of recovered transformants. Therefore the entire process, from embryo isolation to product development, is improved due to a higher return for the amount of effort invested.

Callus is a relatively undifferentiated tissue consisting for the most part of parenchymatous cells. Tissues from various organs from many species of plants can be induced to form callus. Once a plant has been induced to form callus, the callus tissue can be used as an experimental system to investigate and solve a broad range of basic research problems, and to introduce foreign genes into a variety of horticultural and agronomic plants for the purpose of crop improvement.

In monocot tissue culture, embryogenic callus refers to callus that has the potential to regenerate plants. Embryogenic callus is also described as either Type I or Type II. Type I callus is compact, opaque, relatively slow growing, structurally complex, but capable of long-term regeneration either by organogenesis or embryogenesis. Type II callus is friable, rapidly growing, structurally less compact with more clearly formed somatic embryos often consisting of a somatic embryo bome on a suspensor-like structure. Tomes, D. T., p. 175–203. In S. W. J. Bright and M. G. K. (Eds.) Advances in agricultural biotechnology: Cereal tissue and cell culture. Nijhoff/Junk, Boston.) Type I callus is the typical callus formed from many maize genotypes, including many of those that are agronomically important. Unfortunately, Type I is less amenable to transformation than Type II. In plant species other than maize, different terminology, other than Type I and Type II, are used to describe similar callus types.

The present invention allows for callus from a variety of plant species, as well as different types of callus, to be preserved. Examples of plant species from which callus could be preserved include, but are not limited to, maize, wheat, sorghum, soybean, rice, pea, or any plant species capable of forming callus in culture. For example different forms of maize callus could include, but are not limited to, Type I, Type II, leaf base-derived and meristem-derived callus.

The method of cryopreserving plant callus begins by spreading the plant callus evenly on a physical support in order to manipulate the fragile callus with minimal damage. Variation in how thick the callus is spread alters the length of time needed to desiccate the tissue to the desired level. Those skilled in the art can determine the optimal thickness for any particular callus based on the teachings of the present disclosure, without undue experimentation. The physical support could be a glass fiber disc, a paper disc, a fine wire mesh, or any material with similar properties. The plant callus on the support is then grown for four to seven days on a maintenance media containing elevated proline and supplemented with an osmoticum to improve viability of the cells during the freezing process. Typical osmoticums that can be used in the practice of the invention include, but are not limited to, mannitol, sucrose, glucose, polyethylene glycol, sorbitol or any similar compound. Different types of callus will tolerate one osmoticum better than another. Which osmoticum will work best for which callus can be easily determined by the skilled practitioner, in light of the disclosure herein, without undue experimentation. Pre-culture with proline has been previously shown to improve viability of frozen maize cells (Withers, L. A., et al., 1979, Plant Physiol., 64: 675–678).

The physical support containing the cells is then removed from the media and vacuum filtered to remove any free liquid. In order to desiccate the tissue in preparation for freezing, the support with the callus was placed in a chamber which controls humidity. At this stage it is important to control the rate of evaporative dehydration. The final relative humidity and the speed at which this level is reached, and therefore the rate of evaporative dehydration of the cells, is dependent on the method used to control the evaporative rate. Methods to control the rate of evaporative dehydration include, but are not limited to, use of saturated salt solutions including $Ca(NO_3)_2 4H_2O$, $(NH_4)_2SO_4$, or use of any other similar chemical, or any mechanical device that can alter the ambient humidity. The desired rate of evaporative dehydration may vary depending on the tissue that is being desiccated; those skilled in the art can determine the optimal rate for any particular plant callus based on the teaching of the present disclosure, without undue experimentation. In the case of maize and wheat callus, $Ca(NO_3)_2 4H_2O$ and $(NH_4)_2SO_4$ work well to dehydrate callus at the appropriate rate. Generally the cells are removed just as they approach the equilibrium for the specific salt or when they begin to change color and look dry. There appears to be a window in which cell survival is optimum, too wet or too dry, and survival is reduced. Catching the optimum is a combination of empirical timing, observing the cells and monitoring the relative humidity. Again those skilled in the art can determine the optimum based on the teaching of the present disclosure, without undue experimentation. Previous methods of desiccating callus have relied on placing the callus in the presence of silica gel or placing the callus in a laminar flow hood. The present invention has found these methods proved to be inadequate; controlling the rate of evaporative dehydration is important in order to maintain cell viability.

Once the cells have dried, the support with the callus is then placed in storage. For long term storage, submersion in liquid nitrogen is preferable. For shorter periods of time, the callus can be stored at $-80°$ C., $-20°$ C., $4°$ C., or at room temperature. In general, viability will decrease with the higher temperature and the longer the storage time. Storage in liquid nitrogen can apparently maintain cell viability indefinitely.

To revive the plant callus for further use, the plant callus must be thawed. To thaw the callus, it may be placed at room temperature, $4°$ C., $37°$ C., or any convenient temperature which maintains the viability of the callus. Callus from different species may require different thawing temperatures; optimal thawing conditions can be determined based on the instant disclosure without undue experimentation. For maize and wheat callus, room temperature was a convenient temperature which maintained excellent viability. The cells thaw very rapidly at room temperature, usually in about 2–3 minutes.

It will be appreciated by those skilled in the art that other embodiments of the invention may be practiced without departing from the spirit and the scope of the invention as herein disclosed and claimed. For example, a plant callus will tolerate a specific osmoticum, depending on the type of callus and specific species the callus was generated from. Maize Type II callus tolerates manitol well, whereas maize Type I callus maintains viability better on sucrose. The length of pre-treatment before desiccating the tissue will also vary depending on genotype and type of callus. Some types of callus may require a faster or slower dry down time, again depending on genotype and type of callus. Such variations are well within the scope of the present invention, and their determination would not require undue experimentation.

The present invention is further described in the following Examples. The embodiments exemplified hereinafter are in no way to be taken as limiting the subject invention.

EXAMPLE 1

Friable Type II embryogenic maize cultures were initiated by excising immature embryos of maize line Hi-II 10 days after pollination and plating the embryos onto 560P media (see Appendix A for all media recipes). Hi-II was derived by reciprocal crosses between plants of Hi-II Parent A and plant of Hi-II Parent B (both parents available from the Maize Genetic Cooperation Stock Center, Univ. Of Illinois at Chanpaign/Urbana, Illinois.). Seeds recovered from the crosses were termed Hi-II seeds. Hi-II seeds were planted either in a greenhouse or a field. The resulting Hi-II plants were either self-pollinated or cross-pollinated with sister plants. Immature embryos were isolated from ears harvested about 9–13 days after pollination. The embryos were incubated in the dark at 28° C. Developing friable callus was removed from the original explant after 11 days and subcultured to fresh media. The callus was serially subcultured to fresh media every 10–12 days with preferential selection for callus sectors exhibiting rapid growth, a high degree of friability and an early embryogenic morphology. Callus developing from individual embryos were maintained as separate cell lines. Cell lines which did not continue to exhibit the desirable characteristics described above were discarded. Callus cell lines were selected and developed in such a manner for 2–3 months, at which point the morphology and growth characteristics of the callus would begin to stabilize. Cells of this callus type, at this stage, of development are at an optimum in their ability to transform.

In preparation for cryopreservation, callus was harvested at mid point in the subculture cycle, transferred to liquid media and sieved through a mesh screen, preferably a 860 mesh screen. Free liquid was removed from the sieved callus via vacuum filtration. Approximately 250 mg fresh weight of sieved callus was then resuspended in 5 ml of medium and evenly distributed onto a 5.5 cm glass fiber disc via vacuum filtration using a 4.7 cm glass microanalysis holder. The glass fiber filter disc containing the cells was then overlaid on maintenance media (560P) supplemented with 0.2 M manitol and 25 mM proline.

After 4 days culture at 28° C. the filter disc and cells were removed from the media and the free liquid was removed by brief vacuum filtration. The vacuum dried cells were transferred to an empty petri plate which was placed uncovered in a closed container in the presence of a saturated aqueous salt solution. The saturated salt solution, once equilibrium is achieved, maintains a constant relative humidity within the container. The final relative humidity and the speed at which equilibrium is reached, and therefore the rate of evaporative dehydration of the cells, is dependent on the salt used. Both $Ca(NO_3)_2 4H_2O$ (final relative humidity is approximately 50% at 28° C.) and $(NH_4)_2SO_4$ (final relative humidity is approximately 80% at 28° C.) have been used successfully. Water was extracted from the cells by the evaporative dehydration over a period of 2–5 days. In the presence of the saturated $Ca(NO_3)_2 4H_2O$ solution drying took 2–3 days. When the saturated $(NH_4)_2SO_4$ solution was used drying took 4–5 days.

Once dried, the cells were found to be fairly brittle but generally adhered well to the filter disc. The filter discs with attached cells were sliced into about 50×5 mm strips, which were placed into a 1.8 ml cryogenic vial and plunged directly into liquid nitrogen. The frozen samples were transferred to a suitable liquid nitrogen cryofreezer (Crymed Model CMS-450 A) for long term storage.

The cells were revived by removing the vial from the cryofreezer and thawing at room temperature for 2–3 minutes. The filter strips were then transferred to standard maintenance media (560P). Callus so treated is now ready to be transformed or used for any other purpose that calls for maize callus.

Figure 2:
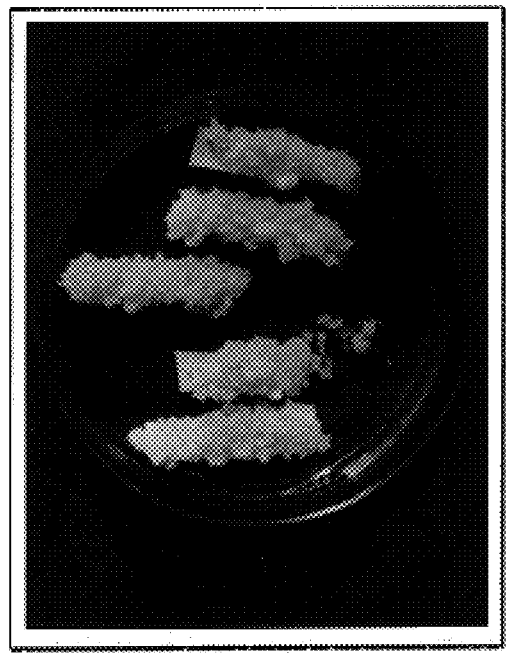
FIG. 2 is a photograph of cryopreserved callus after seven days of growth on maintenance media.

Following the foregoing cryopreservation protocol the callus exhibits normal growth and morphology. FIGS. 1 and 2 show the growth of callus that was cryopreserved according to the foregoing protocol. As can be seen, the callus increased significantly in size within seven days when grown on maintenance media. This rate of growth is typical for friable Type II embryogenic callus. Therefore, the described method of cryopreservation was able to preserve the callus and maintain good cell viability and growth potential.

EXAMPLE 2

Transgenic maize Type II callus from immature embryos of maize line Hi-II was developed as described by Register, J. C., et al., 1994, Plant Molecular Biology 25: 951–961.

The transgenic callus was proliferated by subculturing on 560R media every 12–18 days. In preparation for cryopreservation, callus was collected at mid-point in the subculture cycle and transferred to a 5.5 cm glass fiber filter disc overlaid on maintenance media (560R) supplemented with 0.2 M manitol and 25 mM proline. Approximately 250 mg fresh weight of callus was spread evenly onto each disc.

After 4 days culture at 28° C. the filter disc and cells are removed from the media and the free liquid was removed by brief vacuum filtration. The vacuum dried cells were transferred to an empty petri plate which was placed uncovered in a closed container in the presence of a saturated aqueous salt solution. Use of a saturated salt solution, once equilibrium is achieved, maintains a constant relative humidity within the container. As previously noted, the final relative humidity and the speed at which equilibrium is reached, and therefore the rate of evaporative dehydration of the cells, is dependent on the salt used. Both $Ca(NO_3)_2 4H_2O$ (final relative humidity is approximately 50% at 280° C.) and $((NH_4)_2SO_4$ (final relative humidity is approximately 80% at 28° C.) have been used successfully. Water was extracted from the cells by the evaporative dehydration over a period of 2–5 days. In the presence of the saturated $Ca(NO_3)_2 4H_2O$ solution drying took 2–3 days. When the saturated $(NH_4)_2SO_4$ solution was used drying took 4–5 days.

Once dried, the cells were found to be fairly brittle but generally adhered well to the filter disc. The filter discs with attached cells were sliced into about 50×5 mm strips which were placed into a 1.8 ml cryogenic vial and plunged directly into liquid nitrogen. The frozen samples were transferred to a suitable liquid nitrogen cryofreezer (Crymed Model CMS-450 A) for long term storage.

The cells were revived by removing the vial from the cryofreezer thawing at room temperature and transferring the filter strips to standard maintenance media (560R). Usually the cells thaw very rapidly and are plated after the frost on the cryogenic vial is gone (2–3 minutes). Viability of the callus was good and the transformed callus was then regenerated into plants using methods well known in the art (Fromm, M. E., et al., 1990, Bio/Technology 8: 833–839; Gordon-Kamm, W. J., et al., 1990, The Plant Cell 2: 603–618).

EXAMPLE 3

Embryogenic Type I callus cultures were initiated by excising immature embryos of the maize inbred PHN46 (U.S. Pat. No. 5,567,861 hereby incorporated by reference) 10 days after pollination and culturing the embryos on 605Z media in the dark at 28C. Developing callus was subcultured to fresh media every 3 weeks. In preparation for cryopreservation, 3–5 mm pieces of established embryogenic callus were collected at the mid-point in the subculture cycle and transferred to a 5.5 cm glass fiber filter disc overlaid on 605Z media supplemented with 65 g/l sucrose and 2.88 g/l proline. A thin layer of the modified 605Z media was spread on top of the glass fiber disc to improve the adherence of the callus to the disc and to facilitate the handling of the callus during cryopreservation.

After 1 to 4 days (1–2 days is preferred) of culture on the modified 605Z media the filter disc and cells were removed from the media and the free liquid was removed by brief vacuum filtration. The vacuum dried filter and cells were transferred to an empty petri plate which was placed uncovered in a closed container in the presence of a saturated aqueous salt solution of $Ca(NO_3)_2 4H_2O$. Water was extracted from the cells by evaporative dehydration over a period of 4–5 days.

Once the relative humidity in the chamber had reached 48–78% (78% is preferred) the filter disc with attached cells was sliced into ~50×5 mm strips which were placed into a 1.8 ml cryogenic vial and plunged directly into liquid nitrogen. The frozen samples were transferred to a suitable liquid nitrogen cryofreezer (Crymed Model CMS-450A) for long term storage. The cells were revived by removing the vial from the cryofreezer, thawing at room temperature, and transferring the filter strips to standard maintenance media. The cryopreserved callus exhibited normal growth and morphology. The callus was then transformed. Alternatively, such callus can be used for any other purpose that calls for maize callus.

EXAMPLE 4

Embryogenic callus cultures initiated from immature embryos of the wheat cultivar Bobwhite where developed on 586D media. In preparation for cyropreservation, 3–5 mm pieces of established embryogenic callus were collected at mid-point in the subculture cycle and transferred to a 5.5 cm glass fiber filter disc overlaid on 586D media supplemented with 0.2 M manitol and 25 mM proline. A thin layer of the modified 586D media was spread on top of the glass fiber disc to improve the adherence of the callus to the disc and facilitate the handling of the callus during cryopreservation.

After 4 days of culture on the modified 586D media the filter disc and cells were removed from the media and the free liquid was removed by brief vacuum filtration. The vacuum dried filter and cells were transferred to an empty petri plate which was placed uncovered in a closed container in the presence of a saturated aqueous salt solution of $Ca(NO_3)_2 4H_2O$. Water was extracted from the cells by evaporative dehydration over a period of 3 days, at which time the relative humidity in the chamber was at 59%.

The filter disc with attached cells was removed from the chamber and the filter was sliced into ~50×5 mm strips which were placed into a 1.8 ml cryogenic vial and plunged directly into liquid nitrogen. The frozen samples were transferred to a suitable liquid nitrogen cryofreezer (Crymed Model CMS-450A) for long term storage. The cells were revived by removing the vial from the cryofreezer thawing at room temperature and transferring the filter strips to standard maintenance media. The cryopreserved callus exhibited normal growth and morphology. The callus can now be transformed, or used for any other purpose that calls for wheat callus.

APPENDIX A

605 Z SELECTION MEDIA

| Ingredient | Amount | Unit |
| --- | --- | --- |
| Distilled Deionized $H_2O$ | 900.000 | ml |
| CHU (N6) Basal Salts (Sigma C-1416) | 1.600 | g |
| N6 Macronutrients 10× Stock ## | 60.000 | ml |
| Potassium Nitrate | 1.680 | g |
| B5H Minor Salts 1000× (Sigma C-1416) | 0.600 | ml |
| B5H Fe Na EDTA 100× ### | 6.000 | ml |
| Eriksson's Vitamin Mix (1000X Sigma-1511) | 0.400 | ml |
| S & H Vitamin Mixture 100× Stock (Sigma S-3766) | 6.000 | ml |
| Thiamine .HCL .4 mg/ml | 0.500 | ml |
| Casein Hydrolysate (acid) | 0.300 | g |
| Sucrose | 20.000 | g |
| Glucose | 0.600 | g |
| MES Buffer (Sigma M-8250) | 0.500 | g |
| 2,4-D 0.5 mg/ml | 2.000 | ml |
| Agar (Sigma A-7049, Purified) @ | 8.000 | g |
| DiCamba 1 mg/ml # | 1.000 | ml |
| Silver Nitrate 2 mg/ml # | 0.500 | ml |

Directions:

@ = Add after bringing up to volume
# = Add after sterilizing and cooling to temp.
Dissolve ingredients in polished distilled deionized $H_2O$ in sequence
Adjust to pH 5.8
Bring up to volume with polished distilled deionized $H_2O$ after adjusting pH
Sterilize and cool to 60 C.
## = For 1.0 liter final volume, add 950 mls of distilled deionized $H_2O$, 1.66 g of Calcium Chloride Dihydrate, 4.62 g of Ammonium Sulfate, 4 g of Potassium Phoshphate Monobasic, 1.85 g of Magnesium Sulfate 7-$H_2O$, and 28.3 g of Potassium Nitrate. Dissolve and bring up to volume with distilled deionized $H_2O$.
### = For 1.0 liter final volume, add 950 mls distilled deionized $H_2O$, 3.7 g of Disodium EDTA Dihydrate, and 2.79 g of Ferrous Sulfate 7-Hydrate. Dissolve and bring up to volume with distilled deionized $H_2O$.
Total Volume (L) = 1.00

586 D WHEAT MAINTENANCE MEDIA

| Ingredient | Amount | Unit |
| --- | --- | --- |
| Distilled Deionized $H_2O$ | 950.000 | ml |
| MS Salts (Gibco #11117-074) | 4.300 | g |
| MS Vitamins Stock Solution # | 5.000 | ml |
| 2,4-D 0.5 mg/ml | 3.000 | ml |
| Sucrose | 20.000 | g |
| Gelrite (Sigma P-8169) @ | 2.500 | g |

Directions:

@ = Add after bringing up to volume
Dissolve ingredients in distilled deionized $H_2O$ in sequence
Adjust pH to 5.8 with KOH
Bring up to volume with distilled deionized $H_2O$ after adjusting pH
Sterilize and cool to 60 C.
# = For 1 liter final volume, add 875 mls of distilled deionized $H_2O$, 0.1 g of Nicotinic Acid, 0.02 g of Thiamine.HCl, 0.1 g of Pyridoxine.HCl, and 0.4 g of Glycine. Dissolve ingredients and bring up to volume with distilled deionized $H_2O$.
Total Volume (L) = 1.00

560 R Media

| Ingredient | Amount | Unit |
| --- | --- | --- |
| Distilled Deionized $H_2O$, Filtered | 950.00 | ml |
| CHU (N6) Basal Salts (Sigma C-1416) | 4.000 | g |
| Eriksson's Vitamin Mix (1000× Sigma-1511) | 1.000 | ml |
| Thiamine .HCL .4 mg/ml | 1.250 | ml |
| Sucrose | 30.000 | g |

APPENDIX A-continued

| | | |
|---|---|---|
| 2,4-D 0.5 mg/ml | 4.000 | ml |
| Gelrite (Sigma P-8169) @ | 3.000 | g |
| Silver Nitrate 2 mg/ml # | 0.425 | ml |
| Bialaphos 1 mg/ml # | 3.000 | ml |

Directions:

@ = Add after bringing up to volume
# = Add after sterilizing and cooling to temp.
Dissolve ingredients in distilled deionized $H_2O$ in sequence
Adjust to pH 5.8 with KOH
Bring up to volume with distilled deionized $H_2O$
Sterilize and cool to room temperature
Total Volume (L) = 1.00

560 P Media

| Ingredient | Amount | Unit |
|---|---|---|
| Distilled Deionized $H_2O$, Filtered | 950.000 | ml |
| CHU (N6) Basal Salts (Sigma C-1416) | 4.000 | g |
| Eriksson's Vitamin Mix (1000× Sigma-1511) | 1.000 | ml |
| Thiamine .HCL .4 mg/ml | 1.250 | ml |
| Sucrose | 30.000 | g |
| 2,4-D 0.5 mg/ml | 4.000 | ml |
| L-Proline | 0.690 | g |
| Gelrite (Sigma P-8169) @ | 3.000 | g |
| Silver Nitrate 2 mg/ml # | 0.425 | ml |

Directions:

@ = Add after bringing up to volume
# = Add after sterilizing and cooling to temp.
Dissolve ingredients in distilled deionized $H_2O$ in sequence
Adjust to pH 5.8 with KOH

APPENDIX A-continued

Bring up to volume with distilled deionized $H_2O$
Sterilize and cool to room temp.
Total Volume (L) = 1.00

What is claimed is:

1. A method of cryopreserving plant callus comprising the steps of:

A. spreading the plant callus evenly on a glass fiber disc;

B. culturing the plant callus on a maintenance medium supplemented with mannitol or sucrose, and proline;

C. desiccating the plant callus by exposure to a saturated solution of $Ca(NO_3)_2 4H_2O$ or $(NH_4)_2 SO_4$;

D. placing the desiccated plant callus of (C) free of a cryoprotectant solution in cold storage by immersion in liquid nitrogen; and E. reviving the stored plant callus by thawing the plant callus at room temperature, wherein said stored plant callus shows normal growth and morphology.

2. The method of claim 1 wherein the plant callus is selected from the group consisting of maize, sorghum, wheat, soybean, and rice.

3. The method of claim 2 wherein the plant callus is Type II maize callus.

* * * * *